(12) United States Patent
Evans et al.

(10) Patent No.: US 6,497,656 B1
(45) Date of Patent: Dec. 24, 2002

(54) INTEGRATED WIRELESS BROADBAND COMMUNICATIONS NETWORK

(75) Inventors: Scott Charles Evans, Burnt Hills, NY (US); John Erik Hershey, Ballston Lake, NY (US); David Michael Davenport, Niskayuna, NY (US); Harold Woodruff Tomlinson, Jr., Scotia, NY (US); Ralph Thomas Hoctor, Saratoga Springs, NY (US); Kenneth Brakeley Welles, II, Scotia, NY (US); Stephen Michael Hladik, Albany, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/571,203

(22) Filed: May 16, 2000

Related U.S. Application Data
(60) Provisional application No. 60/180,906, filed on Feb. 8, 2000.

(51) Int. Cl.[7] .................................................. A61B 5/00
(52) U.S. Cl. ........................ 600/300; 128/903; 370/310
(58) Field of Search .............................. 600/300, 301; 128/897–925; 607/32; 380/262; 342/51, 357.06, 450; 370/310, 324, 503, 280

(56) References Cited

U.S. PATENT DOCUMENTS

| | | | | |
|---|---|---|---|---|
| 4,642,424 A | * | 2/1987 | McNair | 380/262 |
| 5,523,760 A | | 6/1996 | McEwan | |
| 5,687,169 A | | 11/1997 | Fullerton | |
| 5,752,976 A | * | 5/1998 | Duffin et al. | 607/32 |
| 5,842,118 A | * | 11/1998 | Wood, Jr. | 342/51 |
| 5,944,659 A | | 8/1999 | Flach et al. | |
| 6,300,903 B1 | * | 10/2001 | Richards et al. | 342/357.06 |

* cited by examiner

Primary Examiner—Eric F. Winakur
Assistant Examiner—David McCrosky
(74) Attorney, Agent, or Firm—Jill M. Breedlove; Christian G. Cabou

(57) ABSTRACT

An integrated tracking, telemetry and local area networking system is provided. A communications system comprises a broadband subsystem comprising at least one UWB node including a first UWB transceiver and at least one application node linked to the UWB node by a broadband link. The system further comprises a wireless subsystem comprising at least one remote communicator, the remote communicator including a second UWB transceiver. The first and second UWB transceivers are configured to communicate with each other via an UWB communications link.

13 Claims, 3 Drawing Sheets

INTEGRATED WIRELESS BROADBAND COMMUNICATIONS NETWORK

This applications claims the benefit of Provisional Application No. 60/180,906, filed Feb. 8, 2000.

BACKGROUND OF THE INVENTION

The invention relates generally to the field of communications, and more particularly, the present invention relates to a wireless telemetry system integrated with a broadband network such as an Ethernet local area network to provide integrated tracking, telemetry and local area networking functions.

Conventional telemetry systems exist that allow data from multiple, remotely located telemeters to be monitored from a central location. These systems typically comprise remote sensors that remotely collect the data from respective devices and transmit the data over a wireless link to a centralized monitoring station. From the centralized monitoring station, the data can be monitored in real time. The station may also include automated monitoring software for alerting an operator whenever a predetermined event occurs, such as a cardiac arrhythmia condition of a remotely monitored hospital patient.

Remote telemeters of conventional telemetry systems are generally of two types: fixed instrument remote telemeters and portable remote telemeters. For example, a remote telemeter for an ambulatory patient is a portable, battery-powered device, also referred to as a tag, which permits the physiologic condition of a patient to be monitored while the patient is ambulatory. The ambulatory telemeter attaches to the patient by a strap or other attachment device, and receives the patient's physiologic data via ECG leads (and/or other types of sensor leads) which attach to the patient's body. The physiologic data is continuously transmitted to the central monitoring station by the telemeter's RF (radio frequency) transmitter to permit real-time monitoring. A design of a remote transceiver which may be used in a two-way, ambulatory telemeter is described in U.S. Pat. No. 5,944,659 to Flach. Examples of fixed instrument remote telemeters include patient telemeters that operate in a similar manner to those described above, but receive the patient's physiologic data from a bedside monitor (or other instrument) over a hardwired link, such as an RS-232 connection. Instrument remote telemeters that transfer the physiologic data to the central station over a hardwired connection are also common.

While such devices are useful for monitoring various conditions of remote objects and persons, e.g., the condition of a patient, they have associated disadvantages. First, typical transceivers in these systems rely upon space, time and frequency diversity schemes to overcome the effects of multi-path interference when transmitting data from a remote device to a monitoring station. Multi-path interference is particularly problematic for intra building transmissions. Implementing diversity schemes such as those mentioned increases the cost, size and complexity of a system. In addition, in at least some implementations, a loss of data may occur when a "switch-over" is performed from one antenna/receiver pair to the other. Another problem encountered in typical distributed antenna systems is that they are typically highly vulnerable to isolated sources of electromagnetic interference (EMI). Specifically, because the signals received by all of the antennas are combined using RF signal combiners, a single source of interference (such as a cellular phone or a faulty preamplifier) at or near one of the antennas can introduce an intolerable level of noise into the system, potentially preventing the monitoring of all patients. One consequence of this problem is that antennas generally cannot be positioned near known intermittent sources of EMI such as X-ray machines, CAT (computerized axial tomography) scanners, and fluoroscopy machines, preventing patient monitoring in corresponding diagnostic areas. Accordingly a need exists for telemetry systems capable of operating reliably indoors with minimal interference and without the need for complex or redundant hardware.

It is frequently desirable to precisely locate and track a remote object whose condition is being monitored. However, while coarse positioning (calculating the position of an object with an accuracy of about a few yards) is possible with existing systems, these systems are not suitable for accurate location and tracking of the remote telemeters from which they receive data. Conventional direction finding devices exist that locate persons and objects more precisely using triangulation techniques and appropriate transmitters. However, these require additional dedicated hardware, and thus a separate infrastructure from the remote monitoring application. Further, these systems may not be accurate in all conditions, especially in severe multipath environments.

Local area networks for sharing data and application programs, i.e., "applications" among users are common in hospitals, offices and commercial and industrial facilities. LAN architecture provides for a plurality of nodes, typically comprising personal computers, configured to run one or more user applications. The computers are typically interconnected by an infrastructure comprising a broadband link such as Ethernet. The LAN infrastructure includes cabling distributed throughout the facility such that all the computers are coupled to one another. When upgrading a facility to include such capabilities as telemetry, remote monitoring and tracking, it would be desirable to integrate the upgraded capabilities with existing LAN infrastructure within the facility. Accordingly, there is a need for an integrated communications network capable of performing conventional LAN applications and functions while carrying out telemetry, monitoring, and tracking functions.

BRIEF SUMMARY OF THE INVENTION

A communications system comprises a broadband subsystem comprising at least one UWB node including a first UWB transceiver and at least one application node linked to the UWB node by a broadband link. The system further comprises a wireless subsystem comprising at least one remote communicator, the remote communicator including a second UWB transceiver. The first and second UWB transceivers are configured to communicate with each other via an UWB communications link.

DETAILED DESCRIPTION OF THE INVENTION

Definitions

Figure 1:
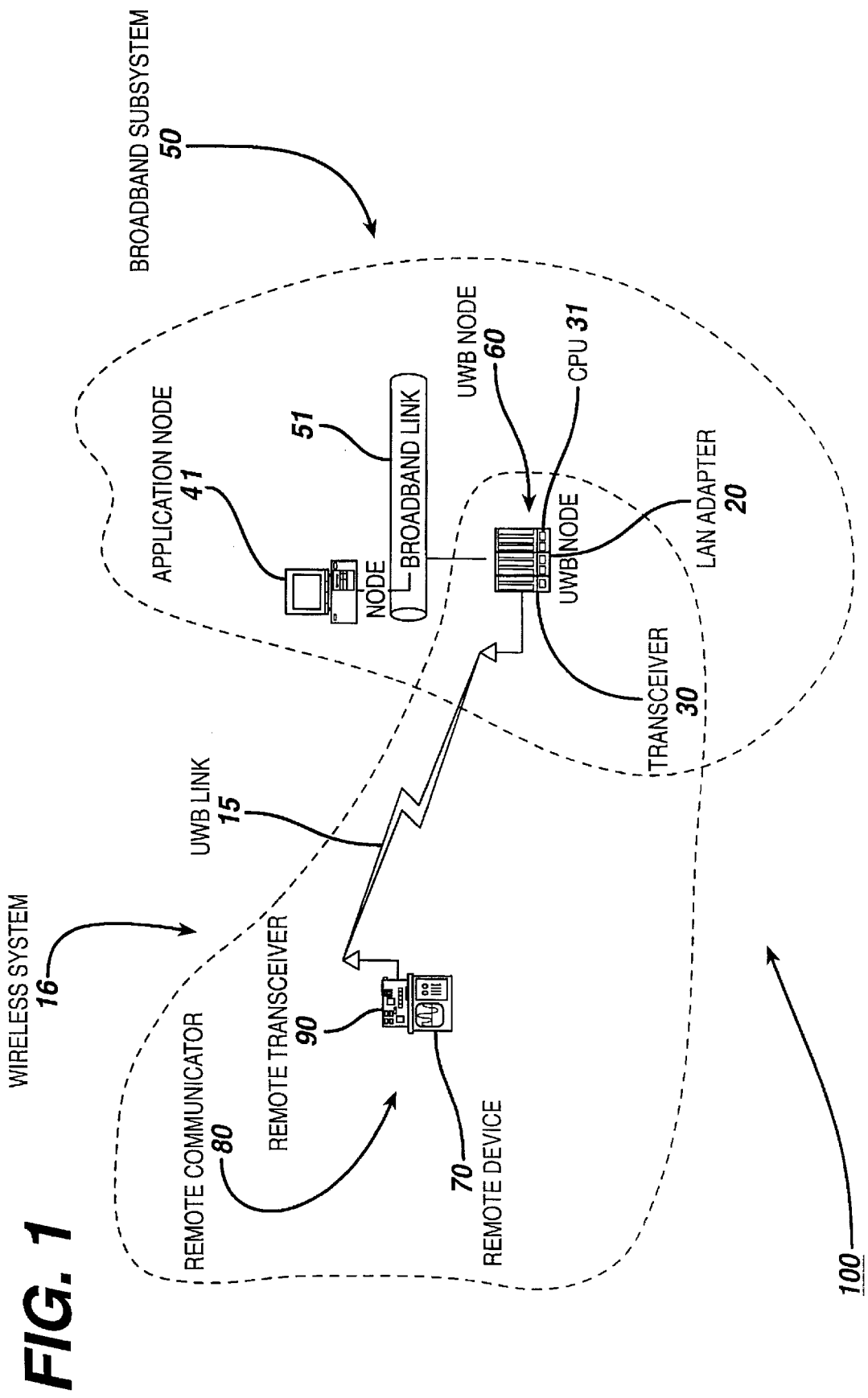
FIG. 1 is a block diagram of a system according to an embodiment of the invention.

For purposes of this specification, the term "ultra wideband" (UWB) as it applies to radio frequency communication technologies refers to a wireless technology for transmitting information by means of a series of ultra short duration pulses, also referred to ultra-wideband pulses. A single bit of information is typically spread over multiple pulses. A UWB pulse is characterized by Gaussian spectral characteristics, that is, energy content distributed generally evenly over a wide range of frequencies, typically at least about 100 MHz at the half power points of a pulse. One example of an UWB pulse has a pulse width of between about 0.2 and about 1.5 nanoseconds and a pulse to pulse interval of between about twenty five and about one thousand nanoseconds.

For purposes of this specification, a "communications system" refers to a collection of individual communications networks, transmission systems, relay stations, and computers configured to operate as an integrated whole. The term "remote" means operating from a distance. The term "local area network" (LAN) refers to a communications system that lies within a limited spatial area and has a specific user group. LANs are typically restricted to relatively small areas, such as rooms, buildings, ships, and aircraft. The term wide area network (WAN) refers to a physical or logical network that provides data communications to a larger number of independent users than are usually served by a LAN. A WAN is usually spread over a larger geographic area than that of a LAN. WANs may include physical networks, such as Integrated Services Digital Networks (ISDNs), X.25 networks, and T1 networks. WANs may be nationwide or worldwide. The "Internet" is a WAN comprising a worldwide interconnection of individual networks operated by government, industry, academia, and private parties. For purposes of this specification the term "node" means a device capable of sending, receiving, or sending and receiving information over a communications channel of a LAN or a WAN network. For purposes of this specification the term "configured" means provided with appropriate components, the components being interconnected and programmed to cooperate in the performance of a given function.

For purposes of this specification, the term "broadband" with respect to a network means network bandwidth capable of supporting multi-media applications such as videoconferencing. The term "broadband" with respect to a signal refers to a signal that occupies a broad frequency spectrum. In general the term "broadband" refers to the property of any communications facility, equipment, channel, or system in which the range of frequencies used for transmission is greater than 0.1% of the mid-band frequency: A "signal" is detectable transmitted energy that can be used to carry information. The term "information" refers to the meaning that a human assigns to data by means of the known conventions used in their representation. The term "information" also refers to unprocessed data of every description which may be used in the production of intelligence.

A "tag" is a self contained, portable device including a transmitter, that is affixed to an object, animal or person to be tracked. The object is tracked based on the information transmitted by the transmitter. A "network interface card" (NIC) is any device configured to communicate digital data between the computer to which it is coupled and a remotely located computer network, for example, to a LAN, by means of a wireless communications link. A "monitor" is any device that collects data, for example physiologic data of patients, and transfers the data to a data distributor, for example a local area network (LAN) 50, over a wireless communications link.

System Overview

Ultra wideband radio broadcasts precisely timed pulses across a very wide frequency spectrum. The UWB radio transmitter and receiver are coordinated to send and receive pulses with, in some cases, an accuracy in the range of trillionths of a second. On any given frequency band that may already be in use, the ultra-wideband signal has power no greater than the normal and anticipated background noise thus decreasing the likelihood of interference.

A communications system 100 according to an embodiment of the invention is illustrated in FIG. 1. Communications system 100 comprises at least one broadband subsystem 50 and at least one wireless subsystem 16. Broadband subsystem 50 comprises broadband link 51, at least one application node 41 and at least one UWB node 60. Wireless subsystem 16 comprises at least one remote communicator 80 and at least one UWB node 60.

In the embodiment illustrated in FIG. 1, broadband subsystem 50 comprises a local area network (LAN) configured such that at least one application node 41 is coupled to at least one UWB node 60. In the embodiment of FIG. 1, broadband subsystem 50 is configured in accordance with a typical Ethernet™ link protocol such as 100BaseTx (Ethernet) protocol. In one embodiment of the invention, broadband subsystem 50 and wireless subsystem 16 have at least one component in common, e.g., UWB node 60.

Remote communicator 80 comprises a remote device 70 and an UWB transceiver 90. UWB transceiver 30 and UWB transceiver 90 are configured to communicate with each other via UWB channel 15. In one embodiment of the invention UWB channel 15 comprises a link for transmission of information from device 70 to UWB node 60. In an alternative embodiment of the invention, UWB channel 15 comprises a link for transmission of information from UWB node 60 to remote device 70. In yet another embodiment of the invention UWB channel 15 comprises a full duplex channel for transmission of information to and from UWB node 60 and remote device 70.

UWB node 60

General

UWB node 60 is configured as a gateway between broadband subsystem 50 and wireless subsystem 16. Although only one UWB node 60 is illustrated in FIG. 1, the number of UWB nodes of system 100 is not limited to a single node. Alternative embodiments of the invention include a plurality of UWB nodes. UWB node 60 receives data from at least one remote communicator 80 via ultrawideband link 15. In one embodiment of the invention, an UWB node is configured to support a particular remote communicator device type. For example, in one embodiment of the invention UWB node 60 is configured to support at least one tag. In an alternative embodiment of the invention UWB node 60 is configured to support at least one monitor. In yet another embodiment of the invention, UWB node 60 is configured to support at least one NIC. In another embodiment of the invention, UWB node 60 is configured to support a plurality of communications device types for example, a tag, a monitor and a NIC.

In one embodiment of the invention, each UWB node is assigned a unique identification code and the code is assigned and programmed during manufacture of UWB node 60. An example identification code comprises at least two fields. One field comprises a device number field. This field contains a device number that is unique to a particular device. In one example, the unique device number is a 29 bit binary number. Accordingly, a population of $2^{29}$ unique UWB nodes are accommodated. Another field comprises a device type code. Examples of device type codes are shown in Table 1. As shown in Table 1, a device type code of 001 corresponds to a tag, while a code of 010 corresponds to a monitor. The identification described herein and shown in Table 1 represents a convenient scheme that provides unique identification of UWB nodes while allowing repetition of numbers across communications devices. However, other embodiments of the invention will employ alternative identification schemes, and these remain within the scope of the invention.

TABLE 1

| Device Type Code | Physical Device |
| --- | --- |
| 000 | Hub |
| 001 | Tag |
| 010 | Monitor |
| 011 | Network Interface Card |

Figure 2:
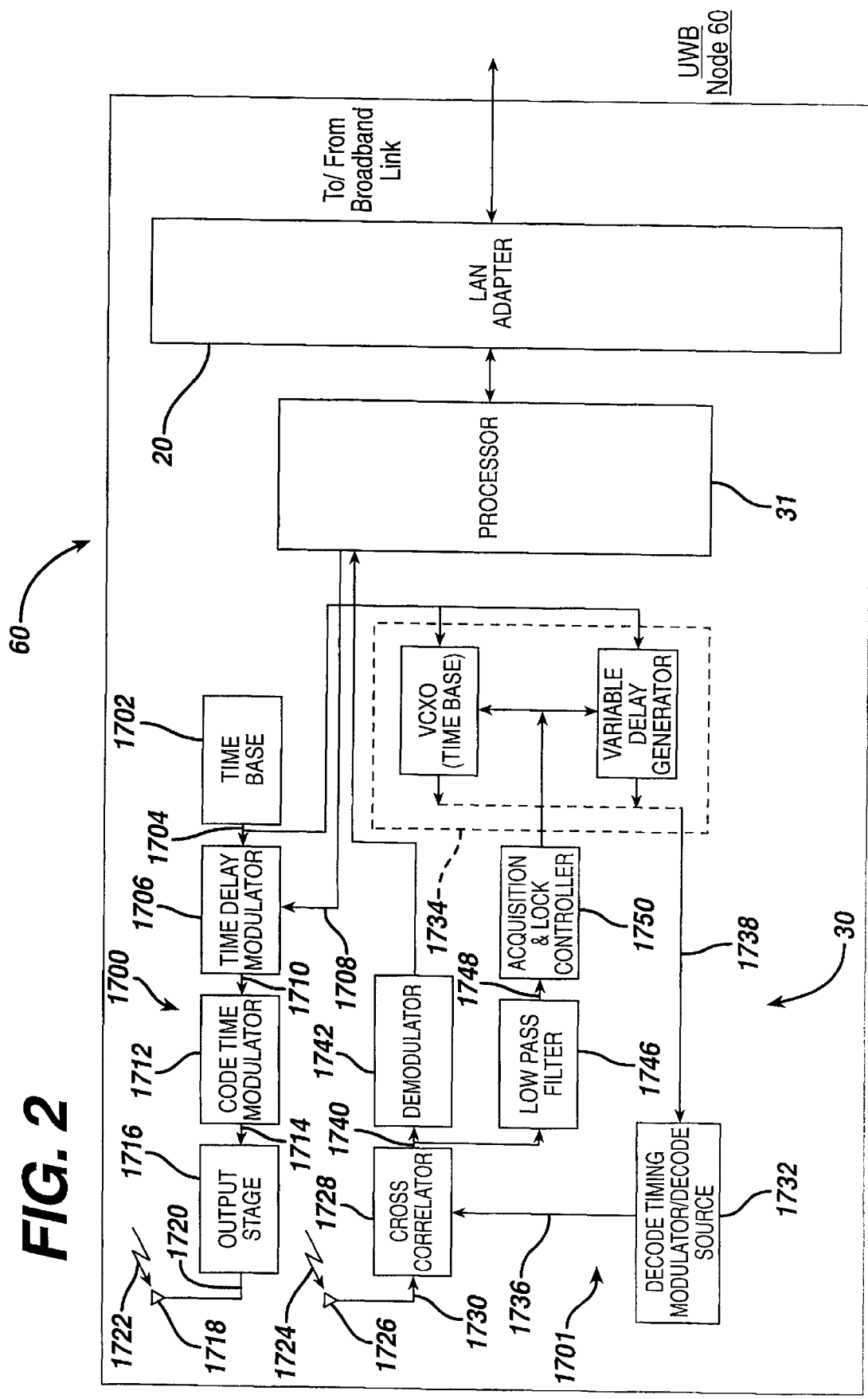
FIG. 2 is a block diagram of an ultra wideband node of the system illustrated in FIG. 1 according to an embodiment of the invention.
Figure 3:
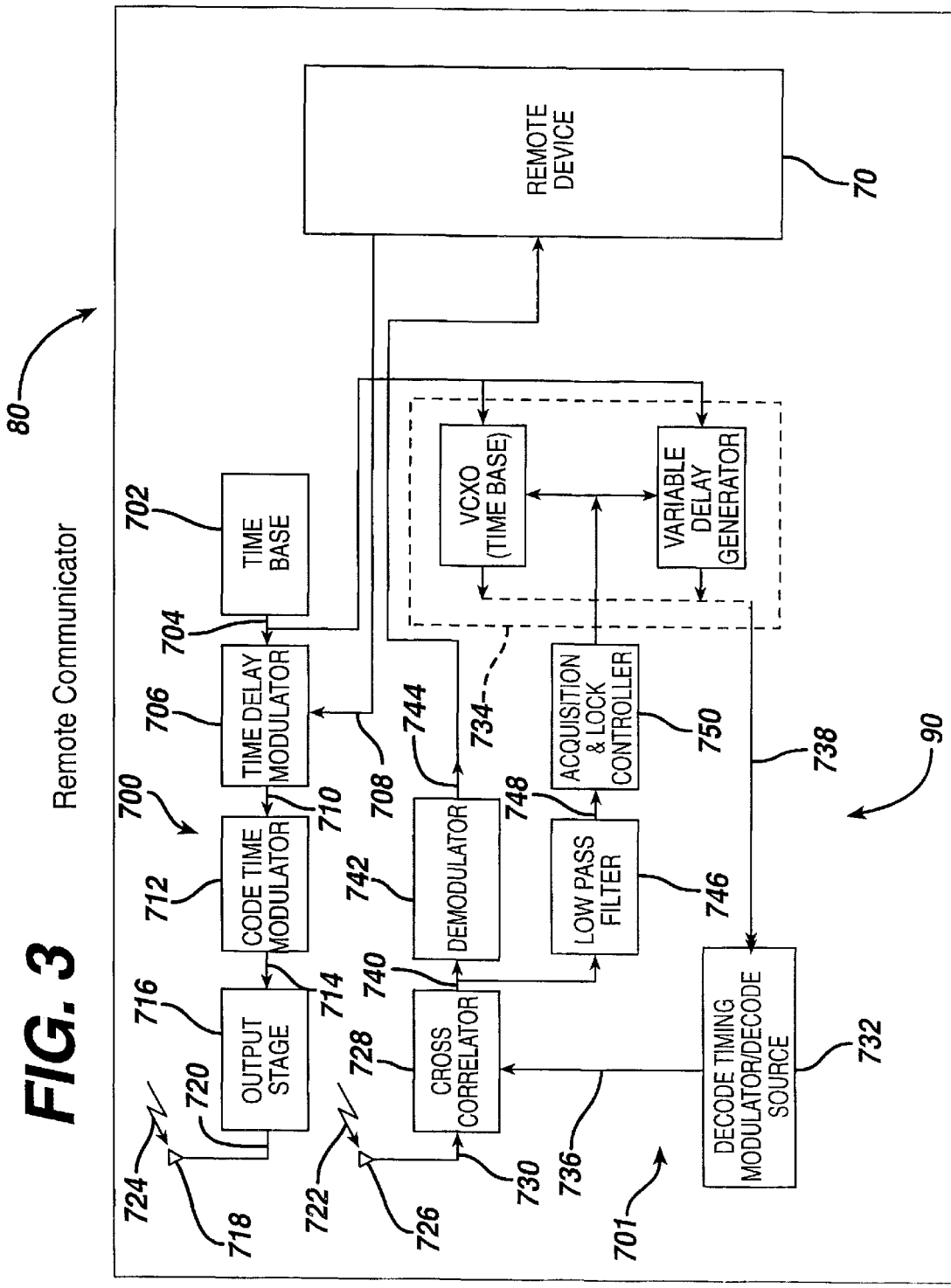
FIG. 3 is a block diagram of a remote communicator of the system illustrated in FIG. 1 according to an embodiment of the invention.

FIG. 2 is a block diagram of UWB node 60 according to an embodiment of the invention. UWB node 60 comprises at least one generic personal computer (PC), for example, a PC comprising a Pentium™ processor 31 that includes typical input output (I/O) circuits and a coupler, e.g., a commercially available LAN adapter 20, configured to couple UWB node 60 to broadband link 51. In one embodiment of the invention LAN adapter 20 and broadband link 51 are configured to operate in accordance with a conventional network architecture standard. Examples of network standards suitable for use in the present invention include peripheral component interconnect (PCI), Industry Standard Architecture (ISA), and Micro Channel Architecture (MCA) and the like. In one embodiment of the invention LAN adapter 20 comprises a commercially available 100BaseTx LAN card.

UWB node 60 further comprises at least one transceiver 30. In one embodiment of the invention UWB transceiver 30 is an impulse radio transceiver configured for full duplex ultra-wideband communications between UWB node 60 and transceiver 90. Other embodiments of the invention are configured for half duplex, or one way communications. An example of a transceiver suitable for use in the present invention is disclosed in U.S. Pat. No. 5687169 to Fullerton. Another example of an UWB receiver can be found in U.S. Pat. No. 5,523,760 to McEwan.

Receiver Portion

First UWB transceiver 30 includes a receiver portion 1701 and a transmitter portion 1700. Receiver portion 1701 is configured to receive a propagated impulse radio signal 1724 transmitted by transceiver 90 of remote communicator 80 (illustrated in FIG. 1). The signal transmitted by remote communicator 80 carries information specific to the application running on application node 41 of broadband subsystem 50. For example, broadband subsystem 50 may be a LAN within a hospital and application node 41 is configured to execute a remote identification program. In that embodiment, remote device 70 is a tag and the signal transmitted by remote communicator 80 contains information about the tagged patient or object.

Receiver portion 1701 is configured to demodulate the signal transmitted by remote communicator 80 and to provide a demodulated signal comprising the transmitted application data and other transmitted application information to processor 31. Processor 31 is programmed to process the data such that the application information is provided to LAN adapter 20 in a format usable by LAN adapter 20.

Receiver portion 1701 further comprises a receive antenna 1726 for receiving propagated impulse radio signal 1724 via UWB channel 15. Signal 1724 is received as an input to a cross correlator 1728 via a receiver transmission line 1730, coupled to the receive antenna 1726. Transceiver 30 further comprises a decode timing modulator/decode source 1732 and an adjustable time base 1734. In one embodiment of the invention, adjustable time base 1734 comprises a voltage controlled oscillator. In an alternative embodiment of the invention, adjustable time base 1734 comprises a variable delay generator. The decode timing modulator/decode source 1732 (hereafter called the decode timing modulator) generates a decode signal 1736 corresponding to the identification code used by the corresponding remote communicator 80 that transmitted the propagated signal 1724. The adjustable time base 1734 generates a periodic timing signal 1738 that comprises a train of template signal pulses having waveforms substantially equivalent to each pulse of the received signal 1724.

The detection process performed by the cross correlator 1728 comprises a cross correlation operation of the received signal 1724 with the decode signal 1736. Integration over time of the cross correlation generates a baseband signal 1740. The baseband signal 1740 is demodulated by a demodulator 1742 to yield a demodulated information signal 1744. The demodulated information signal 1744 contains application specific information provided by remote communicator 80 for use by a corresponding application node 40. Demodulated information signal 1744 is first provided to processor 31. Processor 31 is configured to receive demodulated information signal 1744 and to distribute the information to one or more nodes, for example application node 40, of LAN 50.

In one embodiment of the invention, the baseband signal 1740 is also input to a lowpass filter 1746. The lowpass filter 1746 generates an error signal 1748 for an acquisition and lock controller 1750 to provide minor phase adjustments to the adjustable time base 1734.

Transmitter Portion

As illustrated in FIG. 2, transmitter portion 1700 of transceiver 30 of UWB node 60 comprises a time base 1702 that generates a periodic timing signal 1704, which is provided to a time delay modulator 1706. The time delay modulator 1706 modulates the periodic timing signal 1704 with an information signal 1708.

Information signal 1708 is provided by processor 31. The information represented in signal 1708 is derived from at least one node of LAN 50, for example, application node 40. In one embodiment of the invention, signal 1708 comprises application specific information. For example, in one embodiment of the invention application node 40 comprises a computer running medical application software, and is configured to provide images of a patient to LAN 50 for transmission via UWB channel 15. In that case, signal 1708 carries images. In one embodiment of the invention, the images are transmitted to a remote computer for display to a doctor or other medical operator for evaluation of a condition of a patient. In another example, LAN 50 is located within an industrial facility and application node 40 comprises a maintenance training application. In that case, signal 1708 comprises images and text relating, for example, to removal, repair an installation of equipment.

The modulated timing signal 1710 is provided to a code time modulator 1712 that dithers the modulated timing signal 1710 using a pseudo noise code. The code time modulator 1712 outputs a modulated, coded timing signal 1714 to an output stage 1716. The output stage 1716 uses the modulated, coded timing signal 1714 as a trigger to generate UWB pulses (not shown). The UWB pulses are sent to a transmit antenna 1718 via a transmission line 1720 coupled thereto. The pulses are converted into propagating electromagnetic pulses 1722 by the transmit antenna 1718.

In one embodiment of the invention, the transmitted pulses are encrypted in accordance with a conventional data encryption standard (DES) algorithm. Commercially available devices for data encryption include the Motorola MC6859 DES chip.

Remote Communicator 80

Remote communicator 80 comprises a transceiver 90 coupled to a remote device 70. Remote device 70 is selected from the group including tags, monitors and NICs. In one embodiment of the invention, remote device 70 and transceiver 90 are constructed as an integral unit. In an alternative embodiment remote device 70 and transceiver 90 are separate units coupled together by a communications interface means such as a cable.

While only one remote communicator 80 is depicted in FIG. 1, the invention is not limited to embodiments including a single remote communicator. On the contrary, as those of ordinary skill in the art will recognize, a plurality of combinations and permutations of device types will operate simultaneously in system 100 and will communicate with one or more UWB nodes 60. For purposes of explanation, each type of remote device 70 will be discussed individually hereinbelow.

Remote Devices 70

In one embodiment of the invention, at least one remote device 70 is a tag. In this embodiment at least one application node 41 is configured to execute a computer program for maintaining and managing Radio Frequency Identification (RFID) information. RFID systems are used for identification and/or tracking of equipment, inventory, or living things. RFID systems are radio communication systems that communicate between a radio transceiver and a number of inexpensive remote devices 70.

A tag is a self contained, portable device including a transmitter, that is affixed to an object, animal or person to be tracked. A tag is typically battery powered. Typical users include medical personnel, hospital patients, and visitors to industrial facilities. Tags are typically employed to track users or objects as they move about a facility, or other geographic area.

Tag 70 is coupled to UWB transceiver 90. In one embodiment of the invention, tag 70 is coupled to an UWB transmitter only. In one embodiment of the invention tag 70 includes a motion sensor configured to sense when an object or person is in motion. In that case, transceiver 90 of tag 70 transmits motion data to a corresponding UWB node 60 via UWB link 15. In one embodiment of the invention, Remote communicator 80 is further configured to monitor UWB link 15 for an acknowledgment message from UWB node 60 indicating that motion data has been received from tag 70. If an acknowledgment is not received within a predetermined interval, e.g., an interval no greater than 1% of the tag update rate, remote communicator 80 re-transmits the motion data. An example tag update rate is once every three seconds for mobile tags, and once every 36 seconds for stationary tags. In one embodiment of the invention, acknowledgments from UWB node 60 include error correction and detection codes, and remote communicator 80 is configured to decode and verify acknowledgment integrity.

Remote communicator 80 is configured to confirm that the identification code contained in the acknowledgment matches remote communicator 80's identification code. Remote communicator 80 is configured to discard corrupt or erroneously addressed acknowledgments.

An alternative embodiment of the invention Tag 70 comprises a motion sensor and transceiver 90 transmits data immediately upon tag 70 sensing motion. Transceiver 90 transmits data at a rate greater than the update rate for as long as the object or person is in motion. Upon detecting the cessation of motion for a predetermined time, e.g., least about a 2 minute interval, tag 70 returns to its predetermined tag update rate. In one embodiment of the invention, transceiver 90 is configured to utilize a multiple access (MA) scheme and is assigned an MA channel upon manufacture of remote communicator 80.

In one embodiment of the invention, remote communicator 80 includes an alarm circuit. The alarm circuit is configured to be activated by a user. Example activation mechanisms include mechanical mechanisms such as switches and push buttons, as well as electronic mechanisms such as capacitive switches and the like. The alarm circuit allows a user to request immediate assistance. In one embodiment of the invention, tag 70 includes a spring loaded switch, which, when activated, provides notification that tag 70 has been removed from the object to which it is affixed. In one embodiment of the invention, tag 70 is adapted to sense battery power and to provide an indication of a power supply at or approaching minimum operational levels. Upon receipt of a such a power supply integrity indication, tag 70 provides an indication of the condition via UWB channel 15 to UWB node 60. UWB node 60 provides an indication of the condition to an operator. Examples of indications generated by UWB node 60 include, audible, visual and tactile alarms and indications.

Network Interface Card (NIC)

In one embodiment of the invention, at least one remote communicator 80 includes a NIC transceiver 90. In that embodiment a personal computer such as a lap top computer comprises remote device 70. NIC transceiver 90 is coupled to computer 70 and configured to transmit digital data from computer 70 over UWB link 15 to UWB node 60. NIC transceiver 90 is configured to exchange user data with UWB node 60 in asynchronous, full duplex mode. NIC transceiver 90 is further configured to exchange data packets over UWB link 15 in accordance with a network layer addressing protocol such as an IP protocol. In one embodiment of the invention UWB channel 15 comprises a wireless multiple access (MA) channel configured to convey signals comprising data packets between a UWB node 60 and remote communicator 80.

In one embodiment of the invention, NIC transceiver 90 is assigned a default MA channel upon manufacture. In an alternative embodiment of the invention, the specific UWB channel 15 used by NIC transceiver 90 is selected by UWB node 60. In another embodiment of the invention, the UWB channel is selected by a user. In one embodiment of the invention, NIC transceiver 90 is configured to generate user configurable security codes, and to present these codes to UWB node 60. UWB node 60 is configured to receive and authenticate the user configurable security codes, before UWB node 60 grants NIC transceiver 90 access to broadband subsystem 50. In one embodiment of the invention, NIC transceiver 90 is configured to authenticate itself to UWB node 60 on one channel, and to exchange data on another channel. This configuration allows NIC transceiver 90 to roam between coverage areas of UWB node 60.

In one embodiment of the invention, NIC 90 is adapted to accept input from computer 70 indicating a power supply at or approaching minimum operational levels. Upon receipt of a such a power supply integrity indication, NIC 90 provides an indication of the condition via UWB channel 15 to UWB node 60. UWB node 60 then provides an indication of the condition to an operator. Examples of operator indications include, audible, visual, and tactile alarms and indications.

Monitor

In one embodiment of the invention, remote communicator 80 comprises a battery-powered monitor 70 which attaches to a patient, and which collects the physiologic data of the patient and provides the data to transceiver 90 for transmission to UWB node 60. A monitor is a device which collects data, for example physiologic data of patients (including ambulatory patients) of a medical facility, and transfers the data to a data distributor. Transceiver 90 transmits the physiologic data to broadband subsystem 50 for monitoring and display on an associated application node 40. Transceiver 90 communicates the data to UWB node 60 via UWB channel 15.

As those of ordinary skill in the art will recognize, alternative embodiments of remote communicator 80 and monitor 70 are numerous. For example, in one embodiment of the invention, monitor 70 is configured to monitor occupational exposures of workers. In another embodiment of the invention, monitor 70 is configured as a highly sensitive security badge with both chemical sensing and positional determining capabilities.

Transceiver 90

Each remote communicator 80 includes an UWB transceiver 90. Similar to UWB transceiver 30, UWB transceiver 90 includes a receiver portion 701 and a transmitter portion 700. Receiver portion 701 is configured to receive a modulated signal transmitted by transceiver 30 of UWB node 60 (illustrated in FIG. 1). The modulated signal transmitted by UWB node 60 represents information specific to the application running on application node 41 of broadband subsystem 50.

Receiver portion 701 is configured to demodulate the signal and to provide a demodulated signal comprising commands and data for remote device 70. Receiver portion 701 further comprises a receive antenna 726 for receiving a propagated impulse radio signal 724 via UWB channel 15. Signal 724 originates from UWB node 60 and is received as an input to a cross correlator 728 via a receiver transmission line 730, coupled to the receive antenna 726. Transceiver 30 further comprises a decode timing modulator/decode source 732 and an adjustable time base 734. In one embodiment of the invention, adjustable time base 734 comprises a voltage controlled oscillator. In an alternative embodiment of the invention, adjustable time base 734 comprises a variable delay generator. The decode timing modulator/decode source 732 (hereafter called the decode timing modulator) generates a decode signal 736 corresponding to the identification code used by the corresponding remote communicator 80 that transmitted the propagated signal 724. The adjustable time base 734 generates a periodic timing signal 738 that comprises a train of template signal pulses having waveforms substantially equivalent to each pulse of the received signal 724.

The detection process performed by the cross correlator 728 comprises a cross correlation operation of the received signal 724 with the decode signal 736. Integration over time of the cross correlation generates a baseband signal 740. The baseband signal 740 is demodulated by a demodulator 742 to yield a demodulated signal 744.

In one embodiment of the invention, the baseband signal 740 is also input to a lowpass filter 746. The lowpass filter 746 generates an error signal 748 for an acquisition and lock controller 750 to provide minor phase adjustments to the adjustable time base 734.

Transmit Portion

Transmitter portion 700 of transceiver 90 of remote communicator 80 comprises a time base 702 that generates a periodic timing signal 704, which is provided to a time delay modulator 706. The time delay modulator 706 modulates the periodic timing signal 704 with an information signal 708.

Information signal 708 is provided by remote device 70. In one embodiment of the invention, signal 1708 comprises application specific information. For example, in one embodiment of the invention remote device 70 is a monitor configured to sense the physiologic condition of a patient. In that case, signal 708 carries the patient's physiologic data.

The modulated timing signal 710 is provided to a code time modulator 712 that dithers the modulated timing signal 710 using a pseudo noise code. The code time modulator 712 outputs a modulated, coded timing signal 714 to an output stage 716. The output stage 716 uses the modulated, coded timing signal 714 as a trigger to generate UWB pulses (not shown). The UWB pulses are sent to a transmit antenna 718 via a transmission line 720 coupled thereto. The UWB pulses are converted into propagating electromagnetic pulses 722 by the transmit antenna 718.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A communications system comprising:
    a broadband subsystem comprising at least one UWB node including a first UWB transceiver and at least one application node linked to said UWB node by a broadband link;
    a wireless subsystem comprising at least one remote communicator, said remote communicator including a second UWB transceiver, said first and second UWB transceivers configured to communicate with each other via an UWB communications link;
    said communications system being configured to simultaneously determine via one transmitted signal over the UWB communications link the position in space of a remote object, telemeter data related to said remote object to a node of a local area network, and process said data related to said remote object on one application node of said local area network;
    said communications system being further configured to track the position of said remote object as said object moves through space.

2. The communications system of claim 1 wherein said broadband link is an Ethernet.

3. The system of claim 1 wherein at least one remote communicator comprises a tag.

4. The system of claim 1 wherein at least one remote communicator comprises a monitor.

5. The system of claim 4 wherein said monitor comprises at least one sensor coupled to said UWB transceiver.

6. The system of claim 5 wherein said sensor is configured to sense a physiological condition of a patient.

7. The system of claim 1 wherein at least one remote communicator comprises a network interface card (NIC).

8. The system of claim 1 wherein said object is selected from the group comprising humans, animals, and equipment.

9. The system of claim 1 wherein said wireless subsystem 16 includes a plurality of remote communicators, said plurality including at least one monitor, at least one tag and at least one network interface device.

10. The system of claim 9 wherein said broadband subsystem includes a plurality of UWB nodes, at least one UWB node configured to communicate with said at least one monitor, at least one UWB node configured to communicate with said at least one tag and at least one UWB node configured to communicate with said at least one network interface device.

11. The system of claim 9 wherein at least one UWB node is configured to communicate with said at least one tag, said at least one monitor and said at least one network interface device.

12. The system of claim 1 wherein said application node is configured to execute a radio frequency identification (RFID) application.

13. The system of claim 1 wherein said first and second UWB transceivers are configured to encrypt data to be communicated via said UWB link.

* * * * *